(12) United States Patent
Rambo et al.

(10) Patent No.: US 8,496,007 B2
(45) Date of Patent: Jul. 30, 2013

(54) ASYMMETRICAL AND COMPLEXLY-CURVED, PASSIVE, DEVICE FOR RELIEVING BACK AND SPINAL POSTURAL MECHANICAL PAIN

(76) Inventors: John Rambo, Daly City, CA (US); Vincent Chang, San Francisco, CA (US)

(\*) Notice: Subject to any disclaimer, the term of this patent is extended or adjusted under 35 U.S.C. 154(b) by 624 days.

(21) Appl. No.: 12/383,219

(22) Filed: Mar. 20, 2009

(65) Prior Publication Data

US 2010/0236560 A1 Sep. 23, 2010

(51) Int. Cl.
*A61G 15/00* (2006.01)
*A61H 7/00* (2006.01)

(52) U.S. Cl.
USPC .......... 128/845; 601/134; 606/204; 606/240; 5/652; 5/632

(58) Field of Classification Search
USPC ............. 606/240, 204; 128/845; 602/18, 602/19, 32–33, 35; 601/134, 204; 5/621–624, 5/632–637, 652, 657
See application file for complete search history.

(56) References Cited

U.S. PATENT DOCUMENTS

| | | | | |
|---|---|---|---|---|
| 726,055 A | * | 4/1903 | Hartford | 606/240 |
| 4,230,099 A | * | 10/1980 | Richardson | 606/240 |
| 5,007,414 A | * | 4/1991 | Sexton | 602/19 |
| 5,925,003 A | | 7/1999 | Vincent et al. | |
| 6,159,169 A | * | 12/2000 | Lambden | 601/15 |
| 2005/0131462 A1 | * | 6/2005 | Kalina et al. | 606/240 |
| 2008/0086819 A1 | * | 4/2008 | Valero Pavia | 5/640 |

\* cited by examiner

*Primary Examiner* — Patricia Bianco
*Assistant Examiner* — Kari Petrik
(74) *Attorney, Agent, or Firm* — George S. Cole

(57) ABSTRACT

A device avoiding the use of any motor or perpendicular or rectangular elements, having a convex asymmetrical longitudinal curve, a central longitudinal groove, and mirrored perpendicular and latitudinal, symmetrically-matched convex curves extending from the central groove to the sides, and optimally surfaced with a soft dense foam, uses gravitational force on the body of a user to provide an effective, yet gentle stretch along the length and across the width of the back, particularly at the thoracic vertebrae thereby relieving postural mechanical shoulder, back or spine pain. Additional alternative embodiments using a heating, cooling, or vibrational element along the central longitudinal groove are also described and claimed herein.

4 Claims, 9 Drawing Sheets

-- PRIOR ART --

-- PRIOR ART --

-- PRIOR ART --

ASYMMETRICAL AND COMPLEXLY-CURVED, PASSIVE, DEVICE FOR RELIEVING BACK AND SPINAL POSTURAL MECHANICAL PAIN

BACKGROUND

1A Field of the Invention

This invention is in the field of passive traction devices for the relief and/or prevention of trouble arising from muscular and skeletal distortions induced by tension, forced overextension injury, repetitive strain, situational pressures or other causes to the spinal and back musculature and vertebrae. No external power source (traction motor, vibrational motor, or therapeutic assistant massage) is involved, and the device's operation depends upon the force of gravity upon the body of the user, not gravitational force upon any portion of either the device or accompanying elements.

1B Description of the Related Art

It is a known problem that pain in one's back, shoulder and limbs is sometimes caused by the fact that standing erect causes, over time, shortening of the distances between adjacent vertebra with concurrent squeezing of disks between adjacent vertebra and the resultant compression of nerve endings that cause pain sensation. Additionally, and much more commonly, such pains arise from psychologically-induced muscular tensing ('stress'); from over-extension of some muscles or ligaments and the consequent, reactive and protective tightening; or from repetitive motions and mechanical loads creating muscular tension in the limbs, shoulders, back, and spine. All of the above can be summarized as 'postural or mechanical limb, shoulder, back, or spine pain'.

It is also known that the medical industry has been able to do little to reduce the amount of suffering from postural or mechanical limb, shoulder, back, or spine pain. The body's instinctive, reactive and protective response—to tighten the muscles around a point of pain—can create a vicious feedback cycle that continues to affect the area even after the initial stimulus or cause has been removed or neutralized. Additionally, most people cannot stop their daily activities, or change the elements of their work, home, or social environment(s) that may be creating the stress(es) most responsible for creation of tension in the muscles of their limbs, shoulder, back or spine. Accordingly, most people at some period of their life experience postural or mechanical limb, shoulder, back, or spine pain, and seek assistance from a myriad of remedies for the same.

At present, the main medical remedies consist of drugs, external physical therapy, rest, or (in severe cases) surgery. Drugs prescribed as a remedy may be highly addictive, leaving the patient with a residual problem once such pain has been alleviated; also, there are concerns over dosages and side effects (if they are ingested and/or injected for distribution through internal circulatory means), or difficulties in direct application (if applied as a patch, ointment, or gel) to an area of the body that even affected contortionists may have trouble touching. Those drugs that are muscle relaxants can also impair normal functioning, limit or prevent driving, or the use of potentially-hazardous machinery, and cause the sufferer problems with engaging in normal activities which present any potential hazard, for hours at a time.

Surgery, and external physical therapy, requires trained, expert, clinicians and as such is expensive and dependent upon the availability of such people. Furthermore, treatment and recovery time can be extensive.

Finally, the average person with postural or mechanical limb, shoulder, back, or spine pain often simply cannot afford to rest for the time recommended to fully heal.

Mechanical devices using power sources for providing traction or motion to the limbs, and thus the back or which work by lifting the user's legs, or body, are beyond the field of this invention. While the public domain (consider comedic medical skits) certainly includes the use of passive external weights attached to the limbs via pulleys to provide traction to or through the limbs, these are also beyond the field of this invention.

Purely passive, self-contained, traction devices are both on the market and in the patent literature. Among those currently on the market are the "Lumbar Extender Back Stretcher" (findable by Google search or at Amazon.com; the Health Mark Back Wave II; the True Spineworx Back Realignment Device; and the Stretch Mate Orthopedic Back Stretcher from TVTimedirect. The first two of these are symmetrical along the long axis, while the True Spineworx lacks any side support and has an inner 'dip' along the curve that follows the long axis; these are distinctive elements differentiating them from the present invention. There is also the "Trueback", based on the invention described by Vincent, R. et al., U.S. Pat. No. 5,925,003 (hereinafter Vincent).

All of the above prior art is specifically cited in the accompanying IDS and is not claimed.

1C Differentiation from the Closest Prior Art

Of all the identified and disclosed prior art, only the latter two mentioned (StretchMate and TrueBack) have not already been differentiated above. Both the StretchMate and TrueBack incorporate a significant flaw that reflects an engineering, mechanical viewpoint and overlooks a crucial biological reality, and a blind spot as to the nature of the solution needed.

These two devices, as manufactured items, each contain linear edges and rectangular elements (cf. Vincent, Col. 2, lines 8-11: "a multiplicity of spaced generally rectangular protuberances with each rectangular protuberance being elongated in a direction perpendicular to the axis of elongation of the frame").

Each of these devices focuses on the longitudinal treatment of postural or mechanical limb, shoulder, back, or spine pain—that is, they focus on how the user's back and spine are stretched along their length. But there is a different amount of 'overhang', or unsupported portion of the width of the user's body, along the length of the body; and the corresponding difference in the connective tensions and cantilever stresses that will be experienced as a consequence will interact with the longitudinal stretching. While it is true that, at the scale of treatment, gravity is a planar force, its interaction with the human body placed on top of a device that only partially supports the length and width of the user's body, is not planar in nature. Because people's bodies are both curved, and internally differentiated. Bone and muscle respond differently and are connected, not merely layered, in the body.

The effect on any unsupported portion will be a complex curvature due to the muscular and connective-tissue frictions from the closest supported portions of the body. Placing a significant fraction of one's body over a rectangular element or linear edge, or too sharp a curve (one approximating a linear edge), and extending a further portion of the body (or limb) beyond the linear edge, creates a cantilever weighting and downward stress line at that linear edge. (FIG. 7) When the drop of the unsupported portion of the body is sufficient to pressure the supported portion of the body against the flat surface, the effect will pinch flesh, circulatory vessels, muscle tissue, and nerves along that linear edge. Vincent, in fact, specifically teaches incorporating rectangular protuberances for just that purpose (Vincent, Col. 3, lines 14-16: "The protuberances 29 are designed to put pressure on muscles and nerve endings adjacent the spinal column").

One of the major problems with the prior art is the presence of just such linear edges, ridges, blocks, and other elements that dig into the user's tissues and create a source of discomfort, pain, or counter-acting harm for the user. What is needed is something that makes use of the human body's layering and connectivity to provide more effective, yet gentle, therapeutic stretching of the affected portions.

Another major problem has been the use of uniform or mirror longitudinal curvatures, reflecting the perception that the same amount of pressure will work equally well along all portions of a person's back—even though the stresses, and muscular and skeletal connections, vary between the top cervical and bottom lumbar vertebrae.

Vincent—though it teaches that the first problem is a feature, not a bug—partially addressed this second problem: "a device wherein the curvature of the rows of protuberances along the axis of elongation of the device varies from one end to the other" (Vincent, Col. 2, lines 43-45.) Vincent embeds a partial solution to the problem its inventors identified: "It has been found that exerting pressure on selected regions of the tissues adjacent the spinal column while leaving other areas untensioned allows achievement of enhanced therapeutic results." (Vincent, Col. 3, lines 27-31). But Vincent teaches that pressure must be either present (as it is at each protuberance) or absent (as it is in each recess).

Additionally, the prior art including Vincent has failed to note that the human back is differentially shaped in the second dimension (width)—that is, the direction perpendicular to the axis of elongation and of the spine—and the human body is curved there, also. In fact, the focus of the prior art has remained exclusively on the single, longitudinal axis.

Vincent specifically teaches that adjustment for pressure intensity must be both linearly parallel with the spine (the elongated direction of the device), and intermittent with the pressure ridges. (Vincent, FIG. 5, elements [55] and [57]; Col. 3, lines 61-64: "When the infills 51 and 57 are inserted into the device 10 in the manner described, the upper walls 71 and 73 provide support for soft tissues laterally disposed with respect to the spinal" (Spelling and lack of period in issued patent) Vincent's narrow, uni-dimensional focus can also be seen in that invention's instruction that, "the user lies down lengthways on the device 10 with the spinal column aligned between the rows 25 and 27." (Vincent, Col. 4, lines 31-33.) This invention does not consider, does not attempt to serve, and even worsens, stresses and strains along the lateral dimension—for it incorporates a 90° linear edge on each side (FIG. 1). Its rectangular cross-section (seen from the top on each side) does virtually nothing positive to open up the shoulders or relieve stresses across the width of the back; it does not attempt to address any need for a lateral stretch.

The present invention addresses the problems, issues, and dimension that the prior at and Vincent neither consider or teaches away from. First, it lacks perpendicular elements and linear ridges that dig into a user's back and likely are a source of pain and/or discomfort for the user; and secondly, it does not require the temporary use of 'infills' described in Vincent for the too-sharp rectangular elements. Finally, it addresses concerns and necessities of lateral connectivity and stresses, and provides means to avoid sharp linear element effects that can compromise a truly effective, two-dimensional stretch along and across the body, both the portion supported by the device and the portion(s) not supported by the device.

SUMMARY

A complexly-curved, passive, device for relieving back and spinal postural mechanical pain through passive (gravity) treatment of postural or mechanical limb, shoulder, back, or spine pain, is described herein. By incorporating in the device a length-wise, or longitudinal, complex, convex, and asymmetrical curve, a central concave longitudinal groove, and mirrored complex, convex curves on either side of the central concave longitudinal groove, and (in the preferred embodiment) using a dense soft foam as the surface material, sufficient support is provided for the user's spine and other skeletal elements, while enabling a longitudinal and lateral stretch for the muscles, nerves, and other connective tissues without creating linear pressure lines or pressure points that would otherwise compress or pinch a portion of the user, or otherwise inhibit relaxation and stretching. Simply lying with the affected portion of the body supported by the device, and the remainder curving down to the surface—uses gravity to provide the user with a thorough stretch and massage. By spreading the complex vectors of downward gravitational pull and sideways connective frictions both over a curved, and varying, area, the user's body and tissues are encouraged to relax and open up, thereby effecting a thorough stretch and massage both across the width and along the length of the affected area.

DETAILED DESCRIPTION

Figure 1:
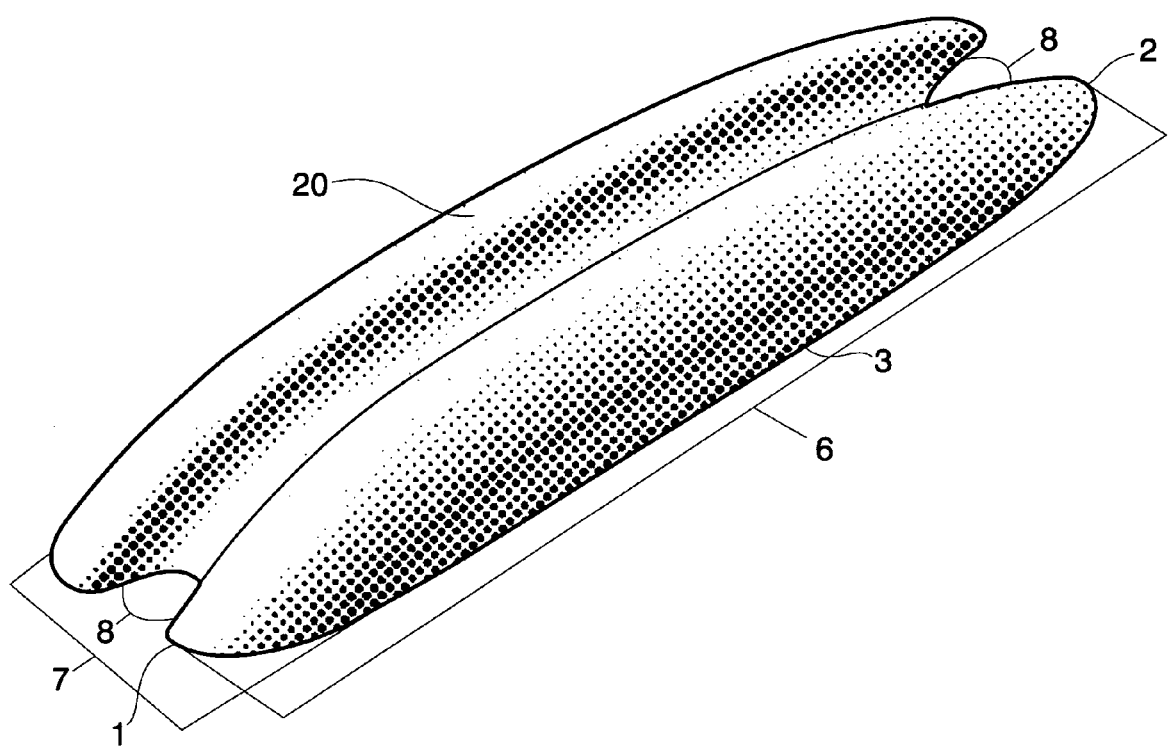
FIG. 1 is a drawing from the top, right perspective of the preferred embodiment of the invention, showing its top surface [20], first end [1] and second end [2] parallel to each other; left side [3], perpendicular to and level with the first end [1] and second end [2]; not visible from this perspective is the right side [4], which is parallel to the left side [3] and also perpendicular to and level with the first end [1] and second end [2]). The device has a long axis [6] between the first end [1] and second end [2], a wide axis [7] between the left side [3] and right side [4], and a central, concave groove [8] running parallel with and centered in the long axis [6] from the first end [1] to the second end [2], and extending not less than one-fifth and not more than one-third of the distance of the wide axis [7]. This view is stippled to show some details of the top surface's convex asymmetric longitudinal curvature along the long axis and complex, symmetric, latitudinal, curvature along the wide axis, each of which are disclosed in more detail below.
Figure 2A:
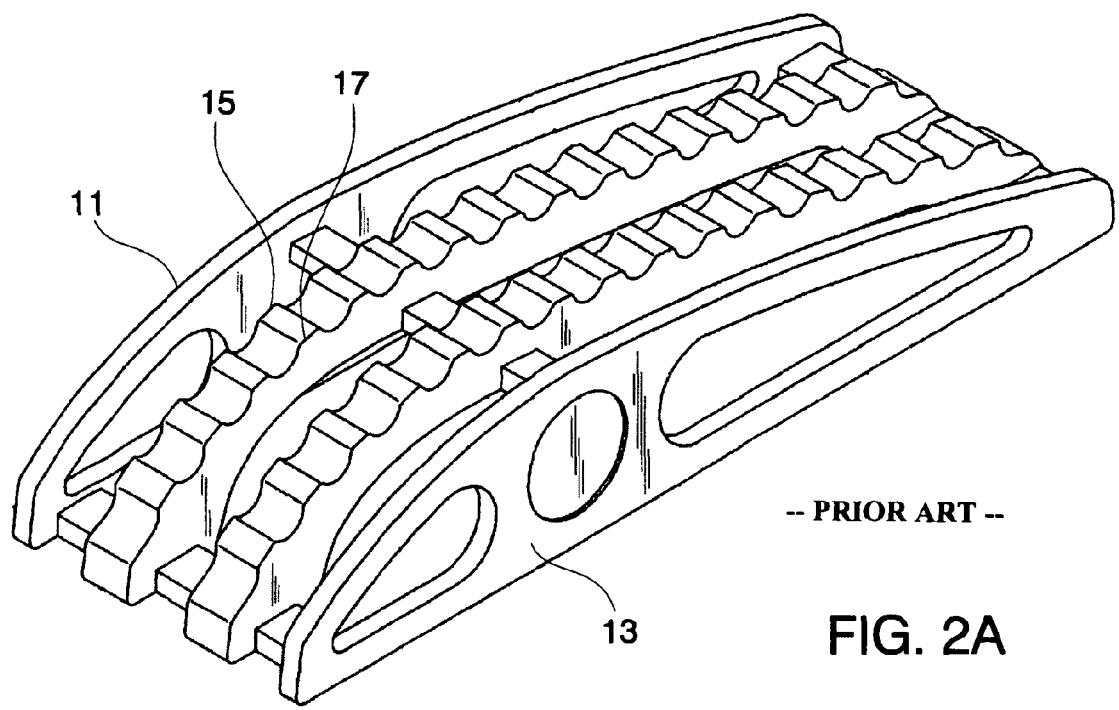
FIGS. 2A and 2B are drawings of the closest prior art showing its rectangularity of sidewalls [11, 13]. These incorporate a rectangular, 90° angle at the top linear edges along the left and right sidewalls and the left and right sidewalls of each of the interior structures [15, 17].
Figure 2B:
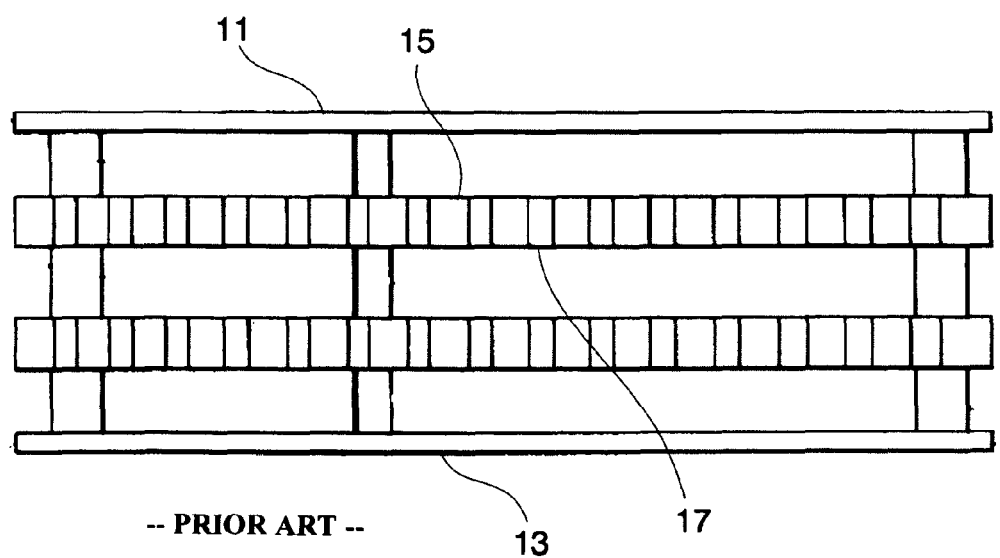
Figure 3A:
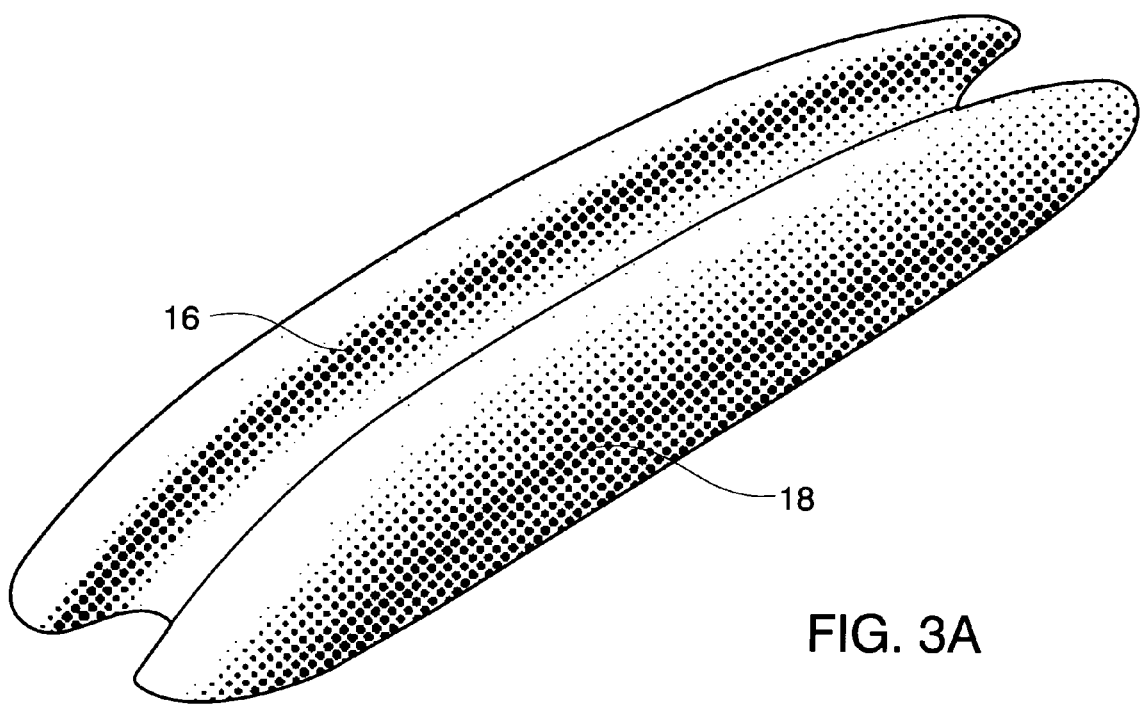
FIGS. 3A and 3B are drawings of the preferred embodiment of the invention using the same perspectives respectively as for FIG. 2A and FIG. 2B, showing the curved and sloping sides [12, 14] of the preferred embodiment of the present invention. Areas of curvature and thus of decreasing pressure and contact are partially indicated (for the right side) by the stippling on FIG. 3A. [16, 18]
Figure 3B:
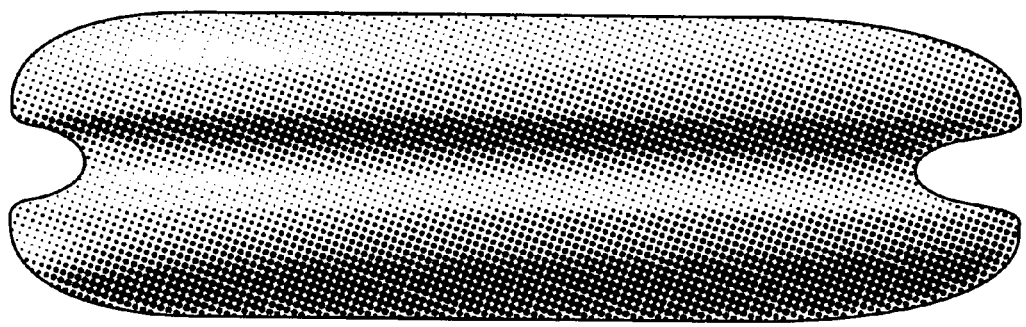
Figure 4:
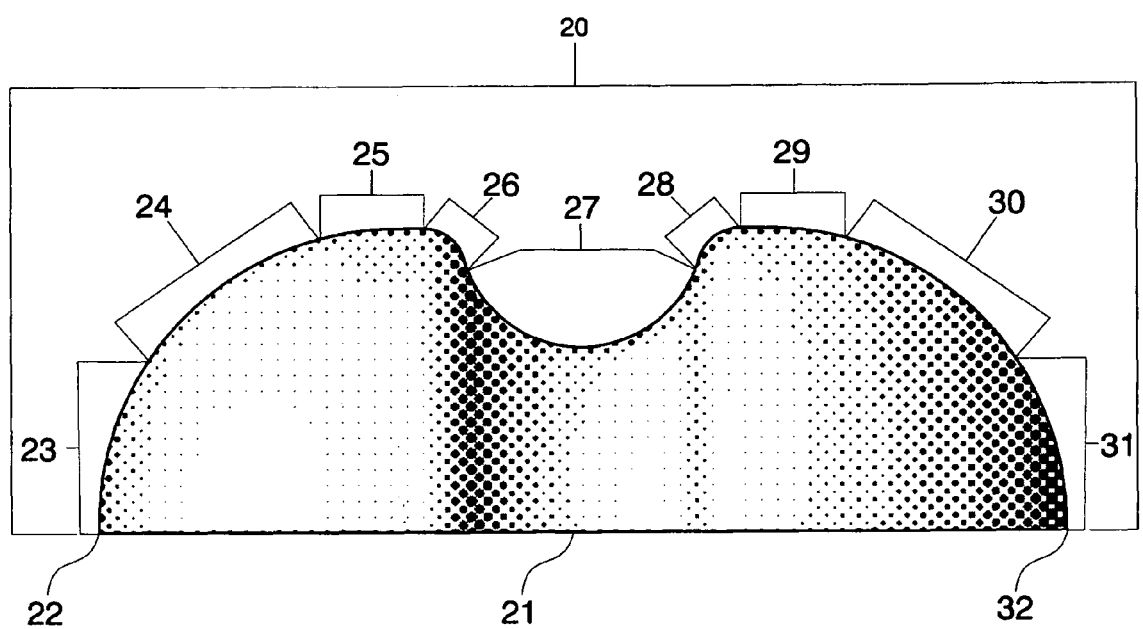
FIG. 4 is a drawing from the front perspective of the preferred embodiment of the invention, showing the complex, symmetric, latitudinal, and continuously varying curvature to the top surface [20] along the wide axis [21]. This curvature begins at the left side [22] with a shallow convex curvature [23], increases to a moderate convex curvature [24], smooths back into a shallow convex curvature [25], then at the beginning of the central, concave groove shifts through a sharp convex curvature [26] to a moderate concave curvature [27] that is centered at a point vertical to the middle of the concave groove, shifts again at the end of the central, concave groove through a sharp convex curvature [28], smooths back into a shallow convex curvature [29], increases to a moderate convex curvature [30], and ends with a shallow convex curvature [31] at the right side [32]. The curves [23-26], [27], and [28-31] thus form a physical palindrome.
Figure 5:
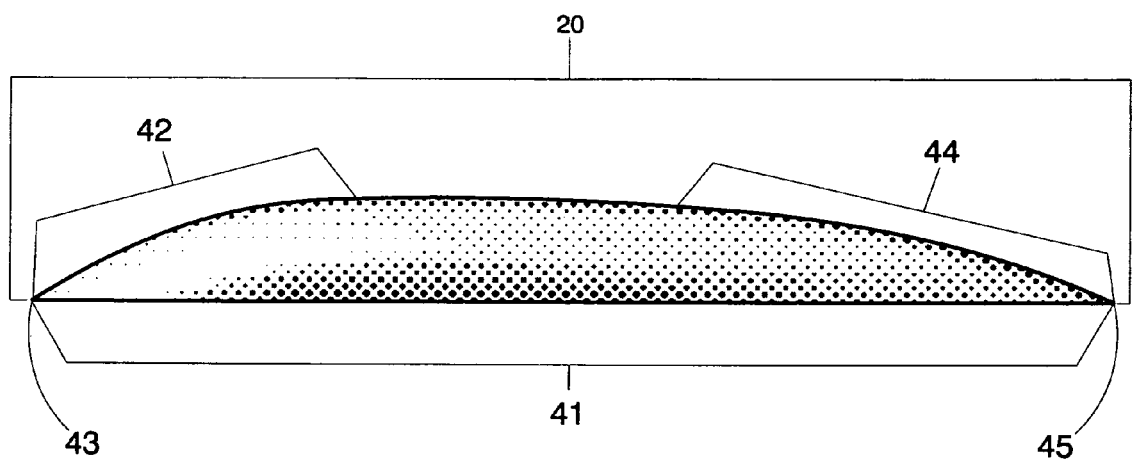
FIG. 5 is a drawing from the side perspective of the preferred embodiment of the invention, showing the convex asymmetric longitudinal curvature to the top surface [20] along the long axis [41] that continuously varies from a relatively small radius of curvature [42] beginning from the first end [43] to a relatively large radius of curvature [44] ending at the second end [45].
Figure 6:
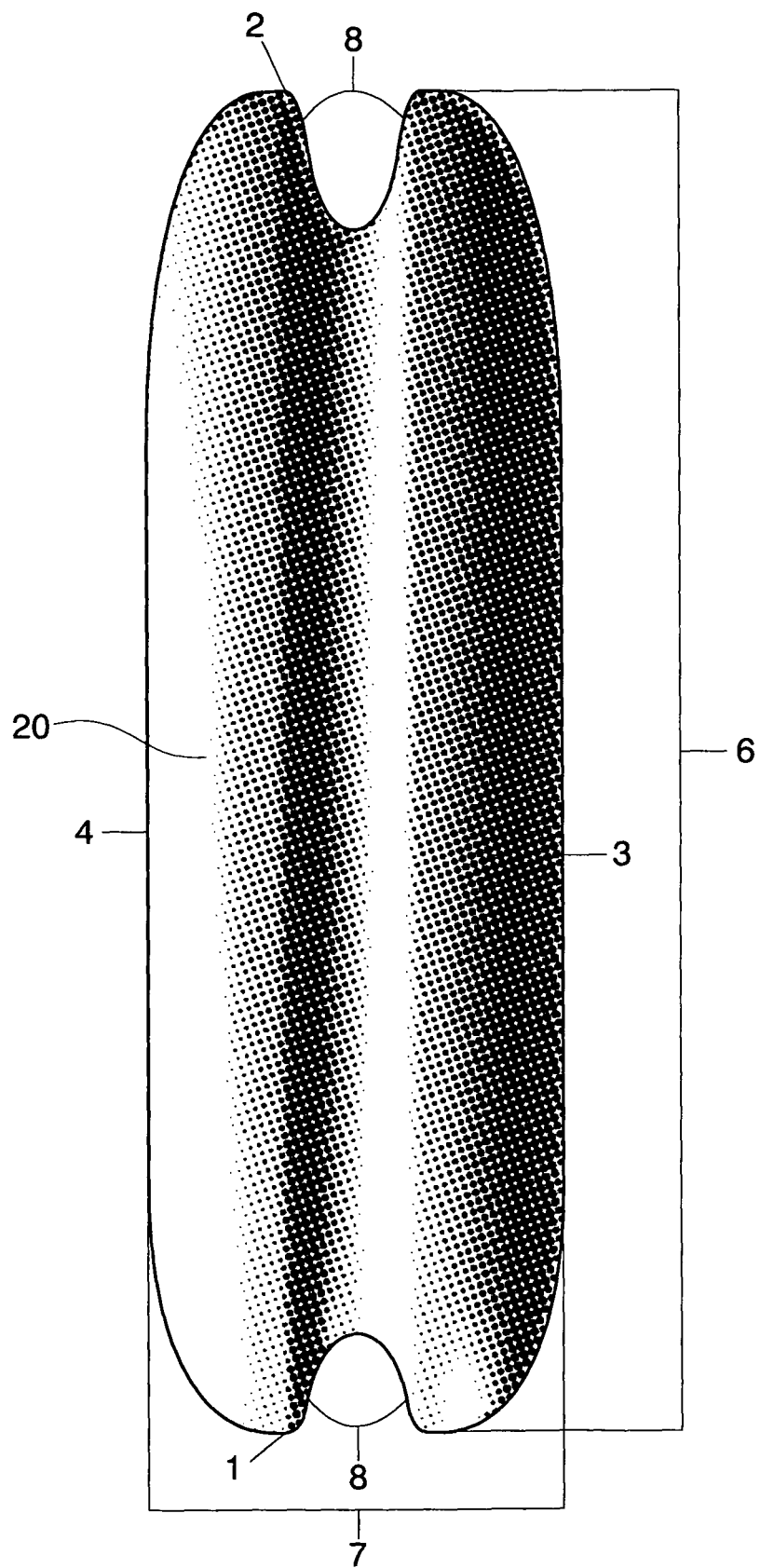
FIG. 6 is a drawing from the top perspective of the preferred embodiment of the invention, showing the complex, symmetric, latitudinal, and continuously varying curvature to the top surface [20] along the long axis [6], including the concave indentation at each end [1, 2] of the central groove [8]. The parallel nature of the left side [3], central groove [8], and right side [4] is also made evident.
Figure 7:
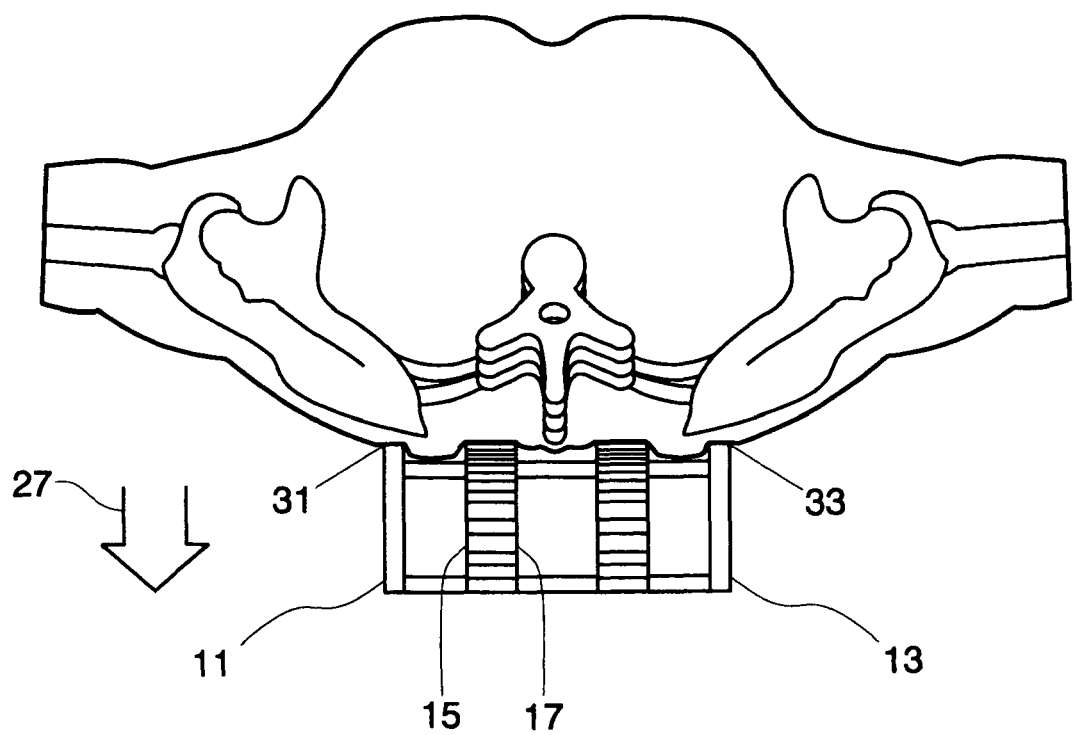
FIG. 7 is a drawing from a top, cross-sectional perspective of a user's torso on the closest prior art (including specifically both the StretchMate and Trueback) showing how the user's shoulders and arms extend beyond the sides of such devices. Gravity is indicated by the vector arrow [27] and is uniform across the horizontal (surface) plane. Each edge [11, 15, 17, 13] is a rectangular (straight vertical) edge, which in use causes a pressure line down the torso, as the combined vectors of gravity and connective friction compress and pinch the user's muscles, nerves and skin against the bones; it is where the abrupt transition of support is most keenly felt. All the prior art's rectangular edges are where the device ceases to support the body, but particularly the side drop-offs create longitudinal pressure lines [31, 33] that not only work against any lateral stretch, but also can negate or diminish beneficial effects of the longitudinal stretch.
Figure 8:
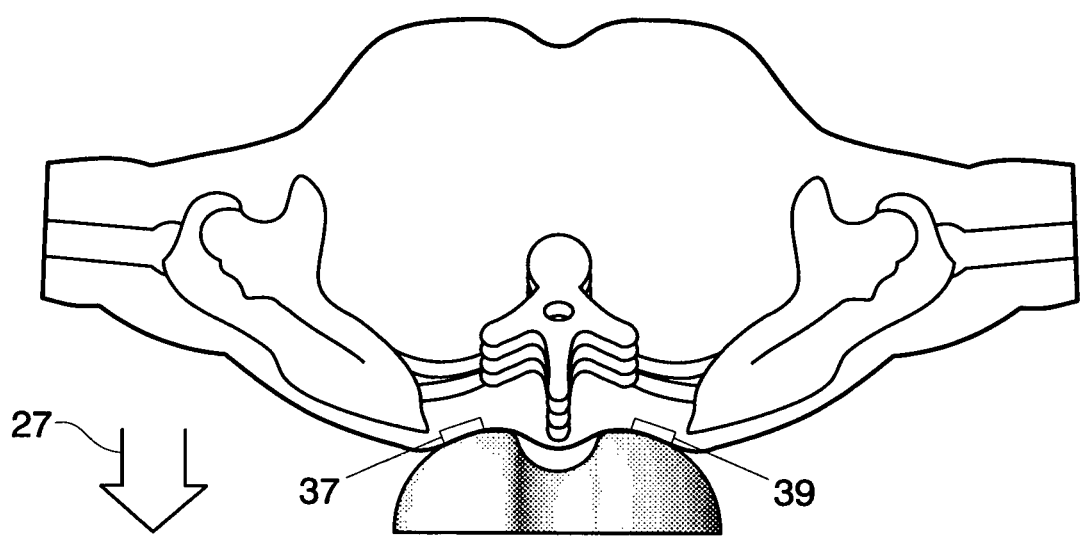
FIG. 8 is a drawing from the same top, cross-sectional perspective of a user's torso on the present invention showing how the shoulders and arm extend along and then beyond its curving sides. Gravity again is indicated by the vector arrow [27]. In contrast to the prior art, however, the present invention replaces the sharp pressure lines at the side-drop offs with areas of distributed relative support [37, 39], from 100% (closest to the spine), to 0% (farthest from the spine). These are the areas over which the pressure is distributed, geometrically reducing the compression and stress on muscle and other tissues, and enabling the lateral stretch without the discomfortable (at best) pressure lines imposed by the prior art.
Figure 9A:
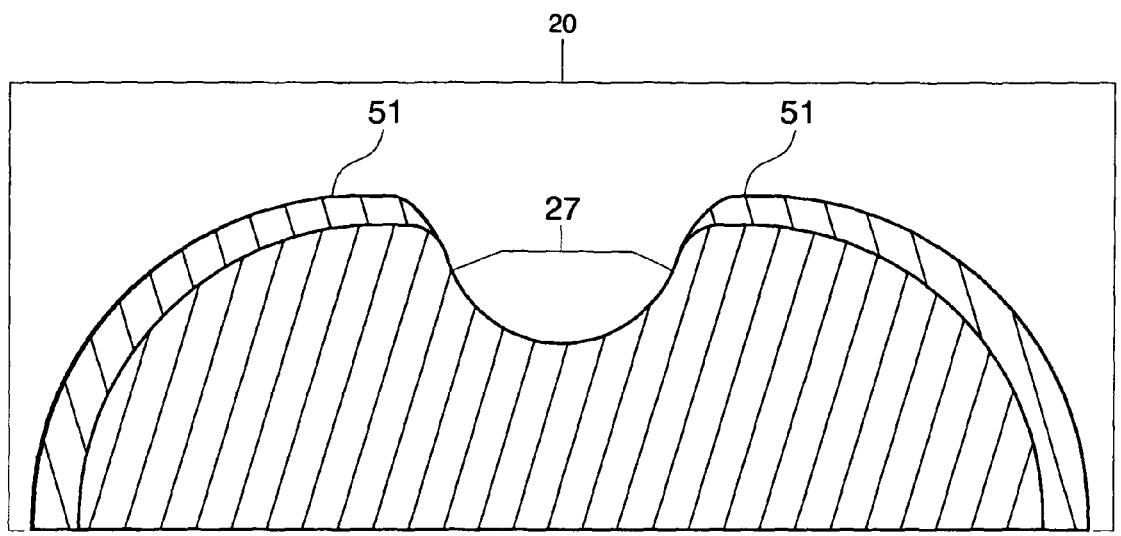
FIGS. 9A and 9B are each a cross-sectional view of an alternative embodiment of the invention with a differential composition, wherein a top layer of a firmly-cushioning substance is attached over a non-yielding harder core. In the first alternative embodiment, shown in FIG. 9A, on either side of the central groove's moderate concave curvature [27], but not within the central groove, the core's top surface [20] is covered by a layer of a firmly-cushioning substance such as a rubber or plastic foam or an aerogel. In the second alternative embodiment, shown in FIG. 9B, the entirety of the core's top surface [20] is covered by a layer of a firmly-cushioning substance such as a rubber or plastic foam or an aerogel.
Figure 9B:
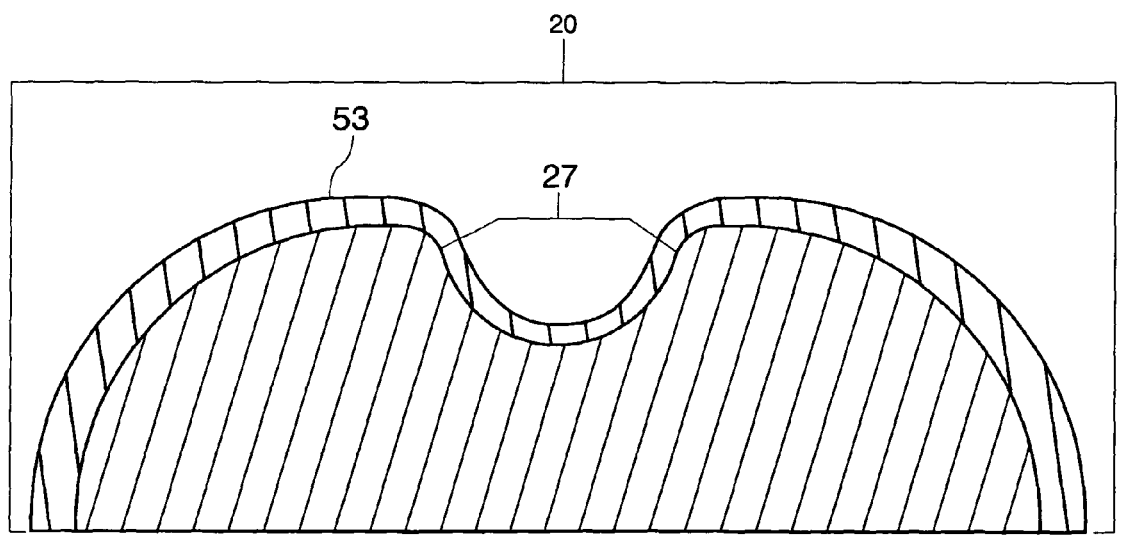

Because the curvature along the spine varies longitudinally not only from person to person, but within each person's spine, the provision of an asymmetric longitudinal form with a sharply-convex and a shallowly-convex portion enables a variety of corrective postures to be adapted by the users of the device. Length-wise asymmetry enables the apex of the curve to be near the C-7 vertebrae or around the lower back (depending on the longitudinal orientation of the sharp convex curve near or far from the user's head).

The present invention addresses the entirely overlooked second (lateral) dimension, that of width. Its use of a complex lateral curvature to the top surface of the device provides a gentle, yet effective stretch to the musculature of the back, shoulders, and spine, without creating a series of pressure lines or points, and distributing the pressure over an area instead of focusing it into a line or point the way a distinct rectangular edge will. These two curves in conjunction with the force of gravity make simply lying on the present invention for as little as a few minutes a day is all that's necessary to provide the user with a thorough thoracic stretch and massage, without creating pressure points or edges that can interfere.

The steep roll-off of the lateral curvature helps to open the shoulders and the scapular area without forcing a tensing strain upon the line of contact between the device and the user's body suspended on its top surface. In a first alternative embodiment of the device, an additional layer of a soft, yet dense cushioning material—a hard-cell, closed foam, or a dense, soft foam, such as cross-linked polyethylene (commonly available commercially) along the top surface, will provide additional buffering without compromising the stretching effects, thereby enabling use even when pressure sores or skin sensitivities (rash, sunburn) might otherwise limit its use. When combined with the asymmetric longitudinal curvature, a great deal of flexibility (which end is used closest to the cervical vertebrae, where the user's thoracic or other vertebrae are positioned longitudinally, whether the shoulders and scapular area are held above the supporting surface or make contact with and are relieved of substantial weight by resting upon the surface after minimal downward movement. In a second alternative embodiment of the device, the top surface of the portion forming the central, concave groove does not have any additional foam layering, to allow deeper flexion laterally and along the central spine of the vertebrae and downward extension of the dorsal tips without supporting contact being made.

This combination of a convex asymmetric curve along the length of the spine and a convex symmetric curve along the width of the shoulders and back enable provision of a more complete and thorough thoracic stretch and support, and facilitate the opening of the shoulder area and distribution of the stretching value across the lateral width of the back. The absence of rectangular side edging, blunt-saw-tooth protuberances, or other linear or rectangular points or lines in the top surface [20] avoids creation of pressure foci that can negate the beneficial effects of the stretch elsewhere, by pinching, stressing, or otherwise creating pain in the supporting muscles and skin pressed against the device by gravity, a definite problem with the prior art. In contrast, this invention designed away as much linearity, angularity and singular points as possibly could be done. The top surface [20] is virtually all curvature. So not only is the invention aesthetically pleasing, but it's smoothness also makes it comfortable to use, hence enticing potential users "back" again and again, thereby providing repeated and effective therapy.

Applying the back to a series of convex curves enables a user to take advantage of the forces of gravity to provide a reverse stretch that is diametrically opposed to the direction in which people generally slouch (head up and forward in conjunction with the rounding of the back length-wise along the spine). By 'diametrically opposed', the stretch induced by using this device is one designed to reverse these bad habits that lead to back pain and stress, i.e. the device simultaneously (1) tilts the head back, (2) arches the back so the chest is pushed forward, and (3) helps create some space between vertebrate.

Because the optimal form for the spine is a column without lateral curvature (from side to side), and because the spine has muscles governing each vertebra's positioning closely adjacent and attaching to the spine, a straight connective column, longitudinally extending through the center of the asymmetric curves, is preferred. The central, concave groove, running parallel with and centered in the long axis and from the first end to the second end, and extending across not less than one-fifth and not more than one-third of the distance of the wide axis, provides a template which the natural pressure of gravity, acting on the body and muscles of the user, uses to establish the optimal non-laterally-deviating spine. Because the key muscles for attachment and adjustment of the individual vertebra run closely to the vertebra, attaching to the tips and running through the 'trenches' paralleling the central spine, the central, concave groove shifts through a sharp convex curvature to a moderate radius of concave curvature that is centered at a point vertical to the middle of the central concave groove, mirrored on the opposite side, to enable pressure to be distributed in a more-closely focused yet still non-linear fashion along and parallel to the spine.

The central, concave groove (~1" deep, ~2" wide) along the length of the device serves multiple purposes. The first is providing open space for protruding vertebrae. A second is to enable pressure to be brought on the musculature adjacent and attaching to the central vertebrae to effect a passive therapeutic massage. A third, mentioned above, is to encourage the maintenance of spinal elongation without lateral curvature.

An additional purpose for the central, concave groove is the provision of a channel to place at least one further element to enhance the devices effectiveness. In one alternative embodiment, this additional element is a cold pack running longitudinally; in a second alternative embodiment, this additional element is a heat pack running longitudinally; in a third alternative embodiment, this additional element is a vibrating pad or element running longitudinally; and in a fourth additional alternative embodiment, this additional element is a combination of more than one of the above (heat, cold, and massage).

While this invention has been described in reference to illustrative embodiments, this description is not to be construed in a limiting sense. Various modifications and combinations described in the illustrative embodiments, as well as other embodiments of the invention will be apparent to those skilled in the art upon referencing this disclosure. It is therefore intended this disclosure encompass any such modifications or embodiments.

The claims stated herein should be read as including those elements which are not necessary to the invention yet are in the prior art and are necessary to the overall function of that particular claim, and should be read as including, to the maximum extent permissible by law, known functional equivalents to the elements disclosed in the specification, even though those functional equivalents are not exhaustively detailed herein. Accordingly, it is intended that the appended claims are interpreted as covering all alterations and modifications as fall within the true spirit and scope of the invention in light of the prior art.

Additionally, although claims have been formulated in this application to particular combinations elements, it should be understood that the scope of the disclosure of the present application also includes any single novel element or any novel combination disclosed herein, either explicitly or implicitly, whether or not it relates to the same invention as presently claimed in any claim and whether or not it mitigates any or all of the same technical problems as does the present invention. The applicants hereby give notice that new claims may be formulated to such features and/or combinations of such features during the prosecution of the present application or of any further application derived therefrom.

We claim:

1. An asymmetrical and complexly-curved, passive, device for relieving back and spinal postural mechanical pain, comprising:
    a) a top surface;
    b) a first end and a second end, parallel to each other;
    c) a left side and a right side, parallel to each other and perpendicular to and level with the first end and second end;
    d) a long axis between the first end and the second end;
    e) a wide axis between the right side and the left side;
    f) a central, concave groove, running parallel with and in the long axis and from the first end to the second end, and both centered in and extending across not less than one-fifth and not more than one-third of the distance of the wide axis;
    g) a convex asymmetric longitudinal curvature to the top surface along the long axis that continuously varies from a relatively large radius of curvature adjacent the first end to a relatively small radius of curvature adjacent the second end;
    h) a complex, symmetric, latitudinal, curvature to the top surface along the wide axis that continuously varies, which begins with a shallow radius of convex curvature at the left side, increases to a moderate radius of convex curvature, smoothes back into a shallow radius of convex curvature, without creating linear pressure lines or pressure points, then at the beginning of the central, concave groove shifts through a sharp convex curvature to a moderate radius of concave curvature that is centered at a point vertical to the middle of the central, concave groove, shifts again through sharp convex curvature at the end of the central, concave groove, smoothes back into a shallow radius of convex curvature, increases to a moderate radius of convex curvature, and ends with a shallow radius of convex curvature at the right side, wherein the device is configured such that a user's shoulders make contact with and extend beyond the sides, thus spreading the complex vectors of downward gravitational pull and sideways connective frictions both over a curved, and varying, area.

2. A device as in claim 1, wherein a top layer of a soft, yet dense cushioning material is attached over a non-yielding core.

3. A device as in claim 1, wherein except for the central, concave groove a top layer of a soft, yet dense cushioning material is attached over a non-yielding harder core.

4. An asymmetrical and complexly-curved, passive, device for relieving back and spinal postural mechanical pain, comprising:
    a) a frame having:
        a first end;
        a second end;
        a long axis between the first and second end;
        a convex asymmetric curvature along the long axis that continuously varies from a relatively large radius of curvature adjacent the first end to a relatively small radius of curvature adjacent the second end;
        a wide axis having a center and two sides, wherein the center is parallel to the long axis, and the sides are perpendicular to the long axis;

b) a single concave groove along the long axis between the first end and second end, said groove comprising at least one-fifth and no more than one-third of the wide axis; and,
c) a complex symmetric curve along the wide axis that continuously varies from a shallow radius of convex curvature at the side, increases to a moderate radius of curvature, smoothes back into a shallow radius of curvature without creating linear pressure lines or pressure points, then shifts at the beginning of the single concave groove to a sharp radius of concave curvature and smoothes into a moderate radius of curvature at the middle of the concave groove, and continues in a mirror-fashion to the other side, wherein the device is configured such that a user's shoulders make contact with and extend beyond the sides, thus spreading the complex vectors of downward gravitational pull and sideways connective frictions both over a curved, and varying, area.

* * * * *